United States Patent [19]

Elbe et al.

[11] Patent Number: 4,487,776

[45] Date of Patent: Dec. 11, 1984

[54] AZOLYL-PHENOXY-TETRAHYDROFURAN-2-YLIDENE-METHANES, A PROCESS FOR THEIR PREPARATION, AND ANTIMICROBIAL AGENTS WHICH CONTAIN THESE SUBSTANCES

[75] Inventors: Hans-Ludwig Elbe, Wuppertal; Manfred Jautelat; /u/ chel BUM, both of Burscheid; Klaus Schaller; Manfred Plempel, both of Wuppertal, all of Fed. Rep. of Germany

[73] Assignee: Bayer Aktiengesellschaft, Leverkusen, Fed. Rep. of Germany

[21] Appl. No.: 461,369

[22] Filed: Jan. 27, 1983

[30] Foreign Application Priority Data

Feb. 11, 1982 [DE] Fed. Rep. of Germany ....... 3204795

[51] Int. Cl.$^3$ .................. A61K 31/41; A61K 31/415; C07D 249/08; C07D 233/56
[52] U.S. Cl. ................. 424/269; 260/465 G; 424/232; 424/273 R; 548/262; 548/336; 549/497; 549/504; 560/51; 568/43; 568/308; 568/325; 568/419
[58] Field of Search ................. 548/262, 336; 424/273 R, 269, 232

[56] References Cited

U.S. PATENT DOCUMENTS 4,259,505 3/1981 Sturm et al. .................. 548/262

Primary Examiner—Alton D. Rollins
Attorney, Agent, or Firm—Sprung, Horn, Kramer & Woods

[57] ABSTRACT

The invention relates to azolyl-phenoxy-tetrahydrofuran-2-ylidene-methanes defined herein under formula (I). Also included in the invention are compositions containing said compounds of formula (I) and methods for the use of such compounds and compositions as antimycotic agents. The invention further includes methods for the manufacture of the compounds of formula (I).

17 Claims, No Drawings

AZOLYL-PHENOXY-TETRAHYDROFURAN-2-YLIDENE-METHANES, A PROCESS FOR THEIR PREPARATION, AND ANTIMICROBIAL AGENTS WHICH CONTAIN THESE SUBSTANCES

The present invention relates to new azolylphenoxy-tetrahydrofuran-2-ylidene-methanes, a process for their preparation, and their use as antimicrobial agents, in particular as antimycotics.

It has already been disclosed that certain azolylalkenols, such as, for example, 1-(imidazol-1-yl)- and -(1,2,4-triazol-1-yl)-2-phenoxy-4,4-dimethyl-pent-1-en-3-oles which are substituted in the phenoxy part, have good antimycotic properties (see DE-OS [German Published Specification] 2,928,968). However, the action of these compounds is not always completely satisfactory.

New azolyl-phenoxy-tetrahydrofuran-2-ylidenemethanes of the formula

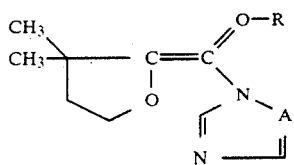

in which A represents a nitrogen atom or the CH group and

R represents optionally substituted phenyl, and their physiologically tolerated acid addition salts have been found.

The compounds of the formula (I) can occur in the form of two geometrical isomers, depending on the arrangement of the groups bonded at the double bond; they are preferentially obtained having a variable ratio of isomers. The present invention relates to the individual isomers as well as the isomer mixtures.

Furthermore, it has been found that the azolyl-phenoxy-tetrahydrofuran-2-ylidene-methanes of the formula (I) are obtained when halogeno-ether ketones of the formula

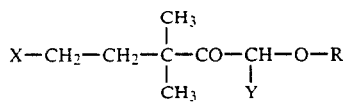

in which

R has the meaning given above and

X and Y represent halogen, preferably chlorine or bromine, are reacted with imidazole or 1,2,4-triazole, in the presence of a diluent and in the presence of an acid-binding agent.

If appropriate, an adduct of the resulting compounds of the formula (I) with an acid can subsequently be formed.

The new azolyl-phenoxy-tetrahydrofuran-2-ylidenemethanes of the formula (I) possess powerful antimycotic properties. In this respect, the compounds according to the invention surprisingly show a generally better activity than the 1-(imidazol-1-yl)- and -(1,2,4-triazol-1-yl)-2-phenoxy-4,4-dimethyl-pent-1-en-3-oles substituted in the phenoxy part, which are known from the prior art and are similar compounds chemically and in terms of their action. The substances according to the invention thus represent an enrichment of medicine.

Formula (I) gives a general definition of the azolyl-phenoxy-tetrahydrofuran-2-ylidene-methanes according to the invention. In this formula, A preferably represents a nitrogen atom or the CH group and R preferably represents phenyl which is optionally monosubstituted to trisubstituted by identical or different substituents, the following being preferably mentioned as substituents: halogen, alkyl having 1 to 4 carbon atoms, alkoxy and alkylthio, each having 1 to 2 carbon atoms, halogenoalkyl, halogenoalkoxy and halogenoalkylthio, each having 1 to 2 carbon atoms and 1 to 5 identical or different halogen atoms, such as fluorine atoms and chlorine atoms, alkoxycarbonyl having 1 to 4 carbon atoms in the alkyl part, nitro, cyano, or phenoxy or phenyl which is optionally substituted by halogen and/or by alkyl having 1 to 2 carbon atoms. Particularly preferred compounds of the formula (I) are those in which A represents a nitrogen atom or the CH group and R represents phenyl which is optionally monosubstituted to trisubstituted by identical or different substituents, the following being preferably mentioned as substituents: fluorine, chlorine, bromine, methyl, ethyl, tert.-butyl, methoxy, ethoxy, methylthio, trifluoromethyl, trifluoromethoxy, trifluoromethylthio, methoxycarbonyl, ethoxycarbonyl, nitro, cyano, and phenoxy or phenyl which is optionally substituted by chlorine and/or methyl. In addition to the compounds mentioned in the preparation examples, the following are additional compounds of the formula (I):

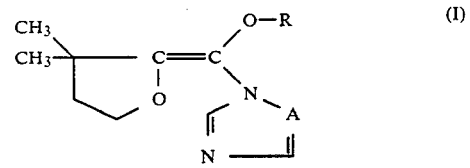

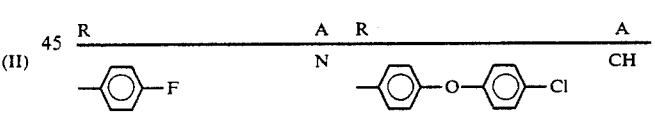

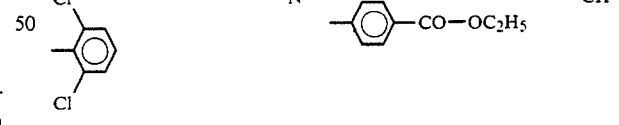

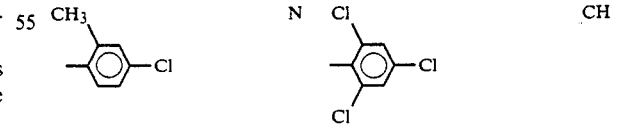

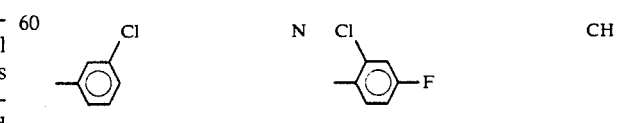

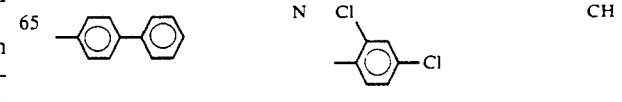

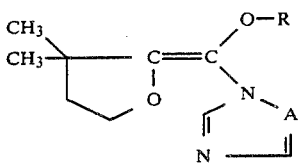

| R | A |
|---|---|
| 4-F-C6H4 with Cl | N |
| 4-CH3-C6H4 | N |
| 4-(4-Cl-C6H4-O)-C6H4 | N |
| 4-(CO-OC2H5)-C6H4 | N |
| 3,4-diCl-C6H3 with Cl | N |
| 3-Cl-4-CH3-C6H3 | N |
| C6H5 | N |
| 3-Cl-4-CH3-C6H3 | CH |
| 4-CH3-C6H4 | CH |

If, for example, 1-bromo-1-(4-chlorophenoxy)-5-chloro-3,3-dimethyl-pentan-2-one and imidazole are used as starting materials, the course of the reaction can be represented by the following equation:

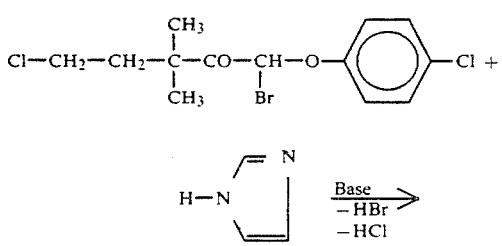

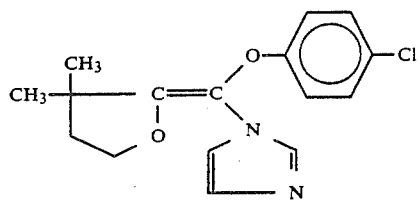

Formula (II) gives a general definition of the halogen-ether-ketones to be used as starting materials in carrying out the process according to the invention. In this formula, R preferably represents the radicals which have already been mentioned in connection with the description of the substances according to the invention, of the formula (I), as being preferred for these substituents.

The halogeno-ether-ketones of the formula (II) are not yet known; however, they can be prepared by known processes, by reacting halogeno-ketones of the formula

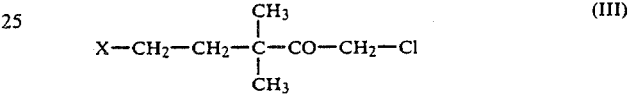

in which

X has the meaning given above, with known phenols of the formula $$H\text{---}O\text{---}R \quad (IV)$$

in which

R has the meaning given above, in a conventional manner, and, in the resulting etherketones of the formula

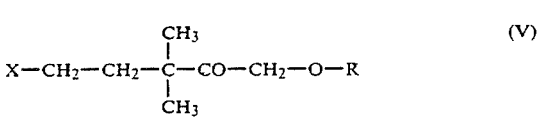

in which

R and X have the meaning given above, exchanging the remaining active hydrogen atom for halogen in a conventional manner (see, also, the preparation examples). The halogeno-ether-ketones of the formula (II) can, if appropriate, be directly reacted further, without being isolated.

The halogeno-ketones of the formula (III) are likewise unknown. They can be obtained in accordance with applicants' German Patent Application P 32 04 788.6 of even filing date corresponding to U.S. application Ser. No. 460,687 filed Jan. 14, 1983 by reacting 2-chloromethylene-3,3-dimethyltetrahydrofuran of the formula

with an acidic compound of the formula $$H\text{---}X \quad (VII)$$

in which

X has the meaning given above, if appropriate in the presence of an inert organic solvent, such as, for example, toluene or methylene chloride, at a temperature between 20° and 150° C.

The 2-chloromethylene-3,3-dimethyltetrahydrofuran of the formula (VI) is likewise not yet known, and likewise forms the subject of Applicants' German Patent Application P 32 04 692.8 of even filing date. It is obtained by successive reaction of 1,1,5-trichloro-3,3-dimethyl-pent-1-ene [see German Patent Application No. P 30 29 270 of Aug. 1, 1980 corresponding to U.S. Ser. No. 281,614 filed July 9, 1981] with carboxylates, such as, for example, anhydrous sodium acetate, and with bases, such as, for example, sodium methylate, in the presence of an inert organic solvent, such as, for example, dimethylformamide, at the reflux temperature.

Suitable diluents for the reaction according to the invention are inert organic solvents. These preferably include ketones, such as diethyl ketone and in particular acetone and methyl ethyl ketone; nitriles, such as propionitrile and in particular acetonitrile; alcohols, e.g. alkanols, such as ethanol or isopropanol; ethers, such as tetrahydrofuran or dioxane; aromatic hydrocarbons, such as toluene or benzene or halogenated aromatic hydrocarbons, such as chlorobenzene; formamides, such as, in particular, dimethylformamide; and halogenated aliphatic hydrocarbons.

The reaction acccording to the invention is carried out in the presence of an acid-binding agent. It is possible to add any customarily usable inorganic or organic acid-binding agent, such as alkali metal carbonate, for example sodium carbonate, potassium carbonate and sodium bicarbonate, or such as lower (e.g. $C_1$–$C_4$) tertiary alkylamines, cycloalkylamines or aralkylamines, for example triethylamine, N,N-dimethylcyclohexylamine, dicyclohexylamine, N,N-dimethylbenzylamine and furthermore pyridine and diazabicyclooctane.

Preferably, an appropriate excess of azole is used.

In the reaction according to the invention, the reaction temperature can be varied within a relatively wide range. In general, the reaction is carried out at between about 20° and about 150° C., preferably at 60° to 120° C.

In carrying out the reaction according to the invention, 1 to 4 mols of azole and 1 to 4 mols of the acid-binding agent are preferably employed per mol of the compound of the formula (II). To isolate the compound of the formula (I), the solvent is distilled off and the residue is worked up in a customary manner.

The compounds according to the invention, of the formula (I), can also be obtained if (a) a halogeno-ketone of the formula (III) is reacted with imidazole or 1,2,4-triazole in accordance with the conditions of the process according to the invention, and the resulting azolyltetrahydrofuran-2-ylidene-methane of the formula

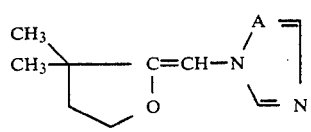 (VIII)

in which

A has the meaning given above, is then first reacted with halogen, in particular with bromine, and thereafter with a phenol of the formula (IV), in each case in a conventional manner;

(b) the 2-chloromethylene-3,3-dimethyltetrahydrofuran of the formula (VI) is reacted in a conventional manner with a phenol of the formula (IV), and the resulting phenoxy-tetrahydrofuran-2-ylidene-methane of the formula

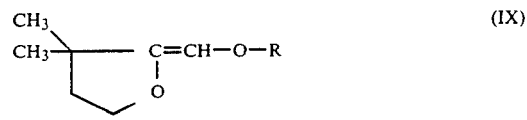 (IX)

in which

R has the meaning given above, is then first reacted in a conventional manner with halogen, in particular with bromine, and thereafter, in accordance with the conditions of the process according to the invention, with imidazole or 1,2,4-triazole.

The azolyl-tetrahydrofuran-2-ylidene-methanes of the formula (VIII) and the phenoxy-tetrahydrofuran-2-ylidene-methanes of the formula (IX) are new; they represent generally interesting intermediate products.

The following acids are preferred for the preparation of physiologically tolerated acid addition salts of the compounds of the formula (I): hydrohalic acids, for example hydrochloric acid and hydrobromic acid, in particular hydrochloric acid, and also phosphoric acid, nitric acid, sulphuric acid, monofunctional and bi-functional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as, for example, p-toluenesulphonic acid and naphthalene-1,5-disulphonic acid. The acid addition salts of the compounds of the formula (I) can be obtained in a simple manner by customary salt formation methods, for example by dissolving a compound of the formula (I) in a suitable inert solvent and adding the acid, for example hydrochloric acid, and can be isolated in a known manner, for example by filtration, and if appropriate purified by washing with an inert organic solvent.

The compounds according to the invention, of the formula (I), and their acid addition salts, display antimicrobial actions, in particular powerful antimycotic actions. They possess a very broad antimycotic action spectrum, especially against dermatophytes and blastomyces as well as biphase fungi, for example against varieties of Candida, such as *Candida albicans,* varieties of Epidermophyton, such as *Epidermophyton floccosum,* varieties of Aspergillus, such as *Aspergillus niger* and *Aspergillus fumigatus,* varieties of Trichophyton, such as *Trichophyton mentagrophytes;* varieties of Microsporon, such as *Microsporon felineum* and varieties of Torulopsis, such as *Torulopsis glabrate.* The listing of these microorganisms in no way implies a limitation of the germs which can be combated but is only of illustrative character.

Examples which may be mentioned of fields of indication in medicine are: dermatomycoses and systemic mycoses caused by *Trichophyton mentagrophytes* and other varieties of Trichophyton, varieties of Microsporon, *Epidermophyton floccosum,* blastomyces and biphase fungi as well as moulds.

The present invention includes pharmaceutical formulations which, in addition to non-toxic, inert pharmaceutically suitable excipients, contain one or more active compounds according to the invention, or which consist of one or more active compound according to the invention, as well a processes for the preparation of these formulations.

The present invention also includes pharmaceutical formulations in dosage units. This means that the formulations are in the form of individual parts, for example tablets, dragees, capsules, pills, suppositories and ampoules, of which the content of active compound corresponds to a fraction or a multiple of an individual dose. The dosage units can contain, for example, 1, 2, 3 or 4 individual doses or $\frac{1}{2}$, $\frac{1}{3}$ or $\frac{1}{4}$ of an individual dose. An individual dose preferably contains the amount of active compound which is given in one administration and which usually corresponds to a whole, a half, a third or a quarter of a daily dose.

By non-toxic, inert pharmaceutically suitable excipients there are to be understood solid, semi-solid of liquid diluents, fillers and formulation auxiliaries of every kind.

Tablets, dragees, capsules, pills, granules, suppositories, solutions, suspensions and emulsions, pastes, ointments, gels, creams, lotions, powders and sprays may be mentioned as preferred pharmaceutical formulations.

Tablets, dragees, capsules, pills and granules can contain the active compound or compounds alongside the customary excipients, such as (a) fillers and extenders, for example starches, lactose, sucrose, glucose, mannitol and silica, (b) binders, for example carboxymethylcellulose, alginates, gelatine and polyvinylpyrrolidone, (c) humectants, for example glycerol, (d) disintegrating agents, for example agar-agar, calcium carbonate and sodium bicarbonate, (e) solution retarders, for example paraffin, and (f) resorption accelerators, for example quaternary ammonium compounds, (g) wetting agents, for example cetyl alcohol and glycerol monostearate, (h) adsorbents, for example kaolin and bentonite, and (i) lubricants, for example talc, calcium stearate and magnesium stearate and solid polyethylene glycols, or mixtures of the compounds listed under (a) to (i).

The tablets, dragees, capsules, pills and granules can be provided with the customary coatings and shells, optionally containing opacifying agents, and can also be of such composition that they release the active compound or compounds only, or preferentially, in a certain part of the intestinal tract, optionally in a delayed manner, examples of embedding compositions which can be used being polymeric substances and waxes.

The active compound or compounds, optionally together with one or more of the abovementioned excipients can also be in a micro-encapsulated form.

Suppositories can contain, in addition to the active compound or compounds, the customary water-soluble or water-insoluble excipients, for example polyethylene glycols, fats, for example cacao fat, and higher esters (for example $C_{14}$-alcohol with $C_{16}$-fatty acid), or mixtures of these substances.

Ointments, pastes, creams and gels can contain, in addition to the active compound or compounds, the customary excipients, for example animal and vegetable fats, waxes, paraffins, starches, tragacanth, cellulose derivatives, polyethylene glycols, silicones, bentonites, silica, talc and zinc oxide, or mixtures of these substances.

Powders and sprays can contain, in addition to the active compound or compounds, the customary excipients, for example lactose, talc, silica, aluminium hydroxide, calcium silicate and polyamide powders or mixtures of these substances. Sprays can additionally contain the customary propellants, for example chlorofluorohydrocarbons.

Solutions and emulsions can contain, in addition to the active compound or compounds, the customary excipients, such as solvents, solubilising agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, especially cottonseed oil, groundnut oil, maize germ oil, olive oil, castor oil and sesame oil, glycerol, glycerol-formal, tetrahydrofurfuryl alcohol, polyethylene glycols and fatty acid esters of sorbitane, or mixtures of these substances.

For parenteral administration, the solutions and emulsions can also be in a sterile form which is isotonic with blood.

Suspensions can contain, in addition to the active compound or compounds, the customary excipients, such as liquid diluents, for example water, ethyl alcohol or propylene glycol, suspending agents, for example ethoxylated isostearyl alcohols, polyoxyethylene sorbitol esters and sorbitane esters, micro-crystalline cellulose, aluminium metahydroxide, bentonite, agar-agar and tragacanth, or mixtures of these substances.

The formulation forms mentioned can also contain colorants, preservatives and additives which improve the odour and flavour, for example peppermint oil and eucalyptus oil, and sweeteners, for example saccharin.

The therapeutically active compounds should preferably be present in the abovementioned pharmaceutical formulations in a concentration of about 0.1 to 99.5, preferably of about 0.5 to 95, % by weight of the total mixture.

The abovementioned pharmaceutical formulations can also contain other pharmaceutical active compounds in addition to the active compounds according to the invention.

The abovementioned pharmaceutical formulations are prepared in the customary manner according to known methods, for example by mixing the active compound or compounds with the excipient or excipients.

The present invention also includes the use of the active compounds according to the invention, and of pharmaceutical formulations which contain one or more active compounds according to the invention, in medicine, for the prevention, alleviation and/or cure of the abovementioned diseases.

The active compounds or the pharmaceutical formulations can be administered locally, orally, parenterally, intraperitoneally and/or rectally, preferably parenterally, and in particular intravenously.

In general, it has proved advantageous in medicine, to administer the active compound or compounds according to the invention in total amounts of about 10 to about 300, preferably 50 to 200, mg/kg of body weight every 24 hours, optionally in the form of several individual administrations, in order to achieve the desired results.

However, it can be necessary to deviate from the dosages mentioned, and in particular to do so as a function of the species and the body weight of the subject to be treated, the nature and severity of the disease, the nature of the formulation and of the administration of the medicament and the time or interval over which the administration takes place. Thus it can in some cases suffice to manage with less than the abovementioned amount of active compound, whilst in other cases the abovementioned amount of active compound must be exceeded. The particular optimum dosage required and the type of administration of the active compounds can easily be determined by anyone skilled in the art on the basis of his expert knowledge.

PREPARATION EXAMPLES

Example 1

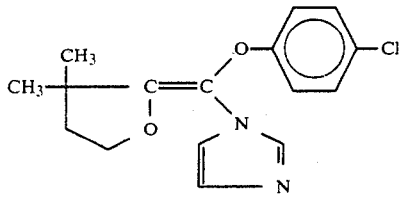

35 g (0.5 mol) of imidazole and 70 g (0.5 mol) of potassium carbonate are dissolved in 700 ml of toluene. 93 g (0.26 mol) of 1-bromo-1-(4-chlorophenoxy)-5-chloro-3,3-dimethyl-pentan-2-one in 200 ml of toluene are added to this mixture at 80° C. The reaction mixture is stirred for a further 10 hours at 90° C., cooled and filtered off under suction from the inorganic residue. The filtrate is washed with water, dried over sodium sulphate and evaporated down. The residue is purified by column chromatography (silica gel: ethyl acetate/cyclohexane=3/1). 12.6 g (14.2% of theory) of (4-chlorophenoxy)-(imidazol-1-yl)-3,3-dimethyltetrahydrofuran-2-ylidene-methane of melting point 85°–88° C. are obtained.

PREPARATION OF THE STARTING MATERIAL

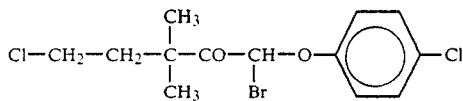

136 g (0.5 mol) of 1-(4-chlorophenoxy)-5-chloro-3,3-dimethyl-pentan-2-one are dissolved in 1,000 ml of methylene chloride. 79.9 g (1 mol) of bromine are added dropwise, at room temperature, in such a manner that the solution is constantly decolourised. Thereafter, stirring is continued for 1 hour at room temperature, and the reaction mixture is concentrated by distilling off the solvent. 1-Bromo-1-(4-chlorophenoxy)-5-chloro-3,3-dimethyl-pentan-2-one is obtained quantitatively, that is to say 177 g, and is directly reacted further.

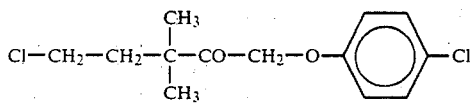

92.5 g (0.72 mol) of 4-chlorophenol and 99.4 g (0.72 mol) of potassium carbonate in 500 ml of toluene are heated under reflux for 2 hours, the water of reaction distilling off azeotropically. The mixture is cooled to 40° C., and 110 g (0.6 mol) of 1,5-dichloro-3,3-dimethyl-pentan-2-one in 300 ml of toluene are added. The reaction mixture is heated at 100° C. for 5 hours, and is then cooled and filtered off under suction from the inorganic residue. The filtrate is washed with dilute sodium hydroxide solution and water, dried over sodium sulphate and evaporated down. 136.3 g (82.6% of theory) of crude 1-(4-chlorophenoxy)-5-chloro-3,3-dimethyl-pentan-2-one are obtained, and this product is directly reacted further.

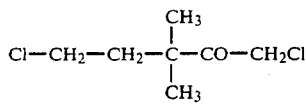

A strong stream of hydrogen chloride gas is introduced, from a cylinder, into 476 g (3.25 mols) of 2-chloromethylene-3,3-dimethyltetrahydrofuran, while cooling with ice. The gas is absorbed completely, and the internal temperature increases to 30° C. After complete saturation with hydrogen chloride, the reaction mixture is stirred for a further 2 hours at room temperature. Excess hydrogen chloride is first drawn off by a water pump, and the mixture is then distilled under a good vacuum. 531 g (90% of theory) of 1,5-dichloro-3,3-dimethyl-pentan-2-one of boiling point 85°–90° C./0.3 mbar are obtained.

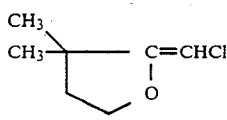

806 g (4 mols) of 1,1,5-trichloro-3,3-dimethylpent-1-ene are heated under reflux for 6 hours with 360 g (4.4 mols) of anhydrous sodium acetate in 1 liter of dimethylformamide. After the mixture has been cooled to approx. 100° C., 1.6 liters (8 mols) of 30% strength sodium methylate solution in methanol are added dropwise, and the mixture is heated under reflux for a further 4 hours. The cold solution is poured into water, and extracted several times with methylene chloride.

After the solution has been dried and the solvent distilled off, 654 g of product remain, and this is fractionated over a column. 522 g (89% of theory) of 2-chloromethylene-3,3-dimethyltetrahydrofuran of boiling point 84°–87° C./20 mbar are obtained.

The following compounds of the formula (I)

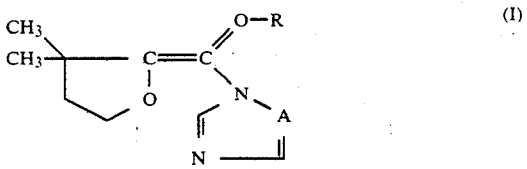

are obtained analogously:

| Example No. | R | A | Melting Point (°C.) or $n_D^{20}$ |
|---|---|---|---|
| 2 | ―⟨⟩―F | CH | 214 |
| 3 | ―⟨⟩(Cl,Cl) | CH | 119 (A form) |

-continued

| Example No. | R | A | Melting Point (°C.) or $n_D^{20}$ |
|---|---|---|---|
| 4 | 2,3-Cl₂-C₆H₃ | CH | 82 |
| 5 | 3-CH₃-4-Cl-C₆H₃ | CH | 109 (A form) |
| 6 | 2-Cl-C₆H₄ | CH | 1.5607 |
| 7 | 4-C₆H₅-C₆H₄ | CH | 95–105 |
| 8 | 2,4-Cl₂-C₆H₃ | CH | 95–105 |
| 9 | 2-Cl-4-F-C₆H₃ | CH | Crystalline mass |
| 10 | 2-Cl-5-F-C₆H₃ | CH | 118 (A form) |
| 11 | 4-Cl-C₆H₄ | N | 124 |
| 12 | 2,4-Cl₂-C₆H₃ | N | Viscous oil |
| 13 | 2,4-Cl₂-C₆H₃ | N | 115–20 (A form) |
| 14 | 2,4-Cl₂-C₆H₃ | N | 1.5578 (B form) |
| 15 | C₆H₅ | CH | 85–90 |

A and B form: the two possible isomeric forms.

USE EXAMPLES

The compounds indicated below are employed as comparative substances in the example which follows:

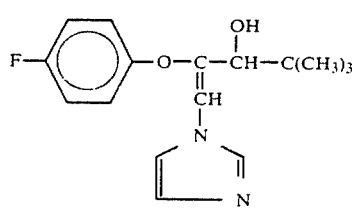 (A)

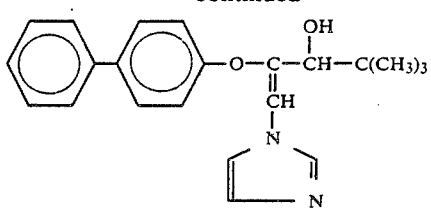 (B)

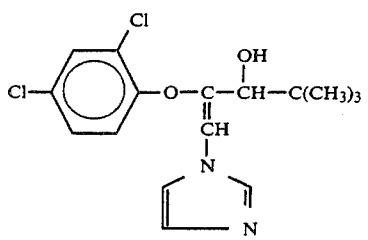 (C)

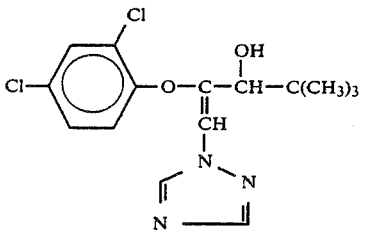 (D)

EXAMPLE A

Antimycotic in vitro activity

Description of the experiment:

The in vitro tests were carried out in a series dilution test with germ inocula of an average of $5 \times 10^4$ germs/ml of substrate. The nutrient medium was (a) for dermatophytes and moulds:

Sabouraud's milieu d'épreuve and (b) for yeasts:

meat extract/glucose broth.

The incubation temperature was 20° C. and the duration of incubation was 24 to 96 hours, in the case of yeasts, and 96 hours in the case of dermatophytes and moulds.

In this test, in particular the compounds of Examples 1, 2, 3, 4, 5, 6, 7, 8 and 11 show a better antimycotic action than the compounds (A), (B), (C) and (D) which are known from the prior art.

TABLE A

Antimycotic in vitro activity

| Active compound | MIC values in γ/ml of nutrient medium in the case of | | | | |
|---|---|---|---|---|---|
| | Trichophyton mentagr. | Microsporum canis | Candida albicans | Torulopsis glabrata | Aspergillus fumig. |
| (A) (known) | 1 | 64 | 32 | 64 | >64 |
| (B) (known) | <1 | 32 | 32 | >64 | >64 |
| (C) (known) | <1 | 32 | 16 | 16 | >64 |
| (D) (known) | <1 | 64 | 32 | 32 | 64 |
| According to Preparation Example | | | | | |
| 1 | <1 | <1 | 8 | 2 | <1 |
| 2 | <1 | <1 | <1 | 2 | 2 |
| 3 | <1 | <1 | <1 | <1 | <1 |
| 4 | <1 | <1 | 16 | 16 | <1 |
| 5 | <1 | <1 | <1 | <1 | 8 |
| 6 | <1 | <1 | 16 | <1 | 2 |
| 7 | <1 | <1 | <1 | <1 | <1 |
| 8 | <1 | <1 | <1 | <1 | <1 |

TABLE A-continued

| | Antimycotic in vitro activity | | | | |
| | MIC values in γ/ml of nutrient medium in the case of | | | | |
| Active compound | Tricho- phyton mentagr. | Micro- sporum canis | Candida albi- cans | Toru- lopsis glabrata | Asper- gillus fumig. |
| 11 | <1 | 16 | 4 | 16 | >64 |

What is claimed is:

1. An azolyl-phenoxy-tetrahydrofuran-2-ylidene-methane of the formula

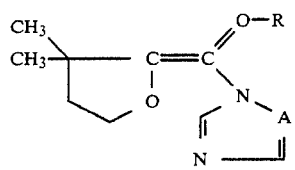
(I)

in which

A represents a nitrogen atom or the CH group and
R represents phenyl which is optionally monosubstituted to trisubstituted by identical or different substituents, selected from halogen, alkyl having 1 to 4 carbon atoms, alkoxy and alkylthio, each having 1 to 2 carbon atoms, halogenoalkyl, halogenoalkoxy and halogenoalkylthio, each having 1 to 2 carbon atoms and 1 to 5 identical or different halogen atoms, alkoxycarbonyl having 1 to 4 carbon atoms in the alkyl part, nitro, cyano, or phenoxy or phenyl which is optionally substituted by halogen and/or by alkyl having 1 to 2 carbon atoms.

2. An azolyl-phenoxy-tetrahydrofuran-2-ylidene methane of claim 1 wherein the halogen atoms in each of halogenoalkyl, halogenoalkoxy and halogenoalkylthio are the same or different and selected from fluorine and chlorine.

3. An azolyl-phenoxy-tetrahydrofuran-2-ylidene-methane of the formula (I) in claim 1, in which A represents a nitrogen atom or the CH group and R represents phenyl which is optionally monosubstituted to trisubstituted by identical or different substituents selected from fluorine, chlorine, bromine, methyl, ethyl, tert.-butyl, methoxy, ethoxy, methylthio, trifluoromethyl, trifluoromethoxy, trifluoromethylthio, methoxycarbonyl, ethoxycarbonyl, nitro, cyano, and phenoxy or phenyl which is optionally substituted by chlorine and/or methyl.

4. A compound of claim 1 which is (4-chlorophenoxy)-(imidazol-1-yl)-3,3-dimethyl-tetrahydrofuran-2-ylidenemethane.

5. A compound of claim 1 which is (4-fluorophenoxy)-(imidazol-1-yl)-3,3-dimethyl-tetrahydrofuran-2-ylidenemethane.

6. A compound of claim 1 which is (2,4-dichlorophenoxy)-(imidazol-1-yl)-3,3-dimethyl-tetrahydrofuran-2-ylidene-methane.

7. A compound of claim 1 which is (4-chloro-2-methyl-phenoxy)-(imidazol-1-yl)-3,3-dimethyltetrahydrofuran-2-ylidene-methane.

8. A compound of claim 1 which is (4-chloro-phenoxy)-(1,2,4-triazol-1-yl)-3,3-dimethyl-tetrahydrofuran-2-ylidene-methane.

9. Process for the preparation of an azolyl-phenoxytetrahydrofuran-2-ylidene-methane of the formula (I) in claim 1, which comprises reacting a halogeno-etherketone of the formula

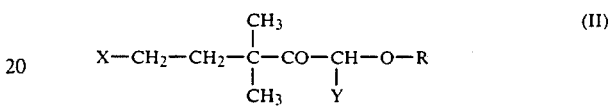
(II)

in which

R has the meaning given in claim 1 and
X and Y represent halogen with imidazole or 1,2,4-triazole, in the presence of a diluent and in the presence of an acid-binding agent.

10. Process of claim 9 wherein X and Y represent chlorine or bromine.

11. A pharmaceutical composition comprising an antimycotically effective amount of a compound of claim 1 in admixture with an inert pharmaceutically suitable excipient.

12. A pharmaceutical composition of claim 11 in the form of a sterile or physiologically isotonic aqueous solution.

13. A medicament in dosage unit form comprising an antimycotically effective amount of a compound of claim 1 in admixture with an inert pharmaceutically suitable excipient.

14. A medicament of claim 13 in the form of tablets, pills, dragees, capsules, ampoules or suppositories.

15. A method for combating mycoses in warm-blooded animals which comprises administering to said animals an antimycotically effective amount of a compound of claim 1 either alone, in admixture with an inert pharmaceutically suitable excipient or in the form of a medicament.

16. A method according to claim 15 in which the active compound is administered in an amount of about 10 to about 300 mg/kg of body weight per day.

17. A method of claim 16 in which the active compound is administered orally.

* * * * *